US008691932B2

(12) United States Patent
Mullins et al.

(10) Patent No.: US 8,691,932 B2
(45) Date of Patent: Apr. 8, 2014

(54) THERMOSETTING MONOMERS AND COMPOSITIONS CONTAINING PHOSPHORUS AND CYANATO GROUPS

(75) Inventors: Michael J. Mullins, Houston, TX (US); Robert E. Hefner, Jr., Rosharon, TX (US); Mark B. Wilson, Clute, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/519,142

(22) PCT Filed: Dec. 22, 2010

(86) PCT No.: PCT/US2010/003234
§ 371 (c)(1),
(2), (4) Date: Jun. 26, 2012

(87) PCT Pub. No.: WO2011/081664
PCT Pub. Date: Jul. 7, 2011

(65) Prior Publication Data
US 2012/0289663 A1 Nov. 15, 2012

Related U.S. Application Data

(60) Provisional application No. 61/284,997, filed on Dec. 30, 2009.

(51) Int. Cl.
*C08G 79/02* (2006.01)
(52) U.S. Cl.
USPC ............. 528/167; 525/420; 525/523; 588/76

(58) Field of Classification Search
USPC ................. 525/420, 523; 588/76; 528/168
See application file for complete search history.

(56) References Cited

U.S. PATENT DOCUMENTS

| 6,180,695 | B1 | 1/2001 | Ito et al. |
|---|---|---|---|
| 6,645,631 | B2 | 11/2003 | Gan et al. |
| 2008/0119630 | A1 | 5/2008 | Bauer et al. |
| 2009/0170983 | A1 | 7/2009 | Tada et al. |
| 2012/0289663 | A1 | 11/2012 | Mullins et al. |

FOREIGN PATENT DOCUMENTS

| CN | 1488672 | 4/2004 |
|---|---|---|
| DE | 19824193 | 12/1998 |
| EP | 1854827 | 11/2007 |
| JP | 5156598 | 6/1993 |
| JP | 2002105160 | 4/2002 |
| JP | 2003041094 | 2/2003 |
| JP | 2003231762 | 8/2003 |
| JP | 2010053085 | 3/2010 |
| KR | 20080052523 | 6/2008 |
| WO | 2005118604 | 12/2005 |

OTHER PUBLICATIONS

International Search Report and Written Opinion from related PCT application PCT/US2010/003234, dated Mar. 23, 2011, 13 pages.

(Continued)

*Primary Examiner* — Shane Fang
(74) *Attorney, Agent, or Firm* — Brooks, Cameron & Huebsch, PLLC

(57) ABSTRACT

A thermosetting monomer comprising at least two of an arylcyanato group and at least two of a phosphorus group.

12 Claims, 2 Drawing Sheets

(56) References Cited

OTHER PUBLICATIONS

Tada, et al. "10H-9-Oxa-10-phosphaphenanthren-10-oxides bearing cyanate groups, their manufacture, resin or polymerizable compositions containing them, and moldings of the compositions", JP2008088079 as XP002627133, 2008, 4 pages.

Ghatge, "Vulcanization of butyl rubber with modified phenol-formaldehyde resins", Elastomerics, Dec. 1979, vol. 111, Issue 12, 48-50.

Persson, et al. "Effects of solvent, water activity and temperature on lipase and hydroxynitrile lyase enantioselectivity", Enzyme and Microbial Technology, vol. 30, 2002, 916-923.

Lin, "Synthesis of novel phosphorus-containing cyanate esters and their curing reaction with epoxy resin", Polymer, 45, Issue 23, 2004, 7911-7926.

International Preliminary Report on Patentability from related PCT application PCT/US2010/003234, dated Jul. 12, 2012, 6 pages.

THERMOSETTING MONOMERS AND COMPOSITIONS CONTAINING PHOSPHORUS AND CYANATO GROUPS

This application is a National Stage application under 35 U.S.C. 371 of PCT/US2010/003234, filed on Dec. 22, 2010 and published as WO2011/81664 A1 on Jul. 7, 2011, which claims the benefit of U.S. Provisional Application Ser. No. 61/284,997 filed Dec. 30, 2009, the entire contents of which are incorporated herein by reference in its entirety.

TECHNICAL FIELD

The present disclosure relates generally to thermosetting monomers, and in particular to thermoset monomers that contain phosphorus and cyanato groups.

BACKGROUND

Synthetic resins are widely used in both industrial and consumer electronics because of among other things, their chemical resistance, mechanical strength and electrical properties. For example, synthetic resins can be used in electronics as protective films, adhesive materials and/or insulating materials, such as interlayer insulating films. To be useful for these applications, the synthetic resins need to provide ease of handling and certain necessary physical, thermal, electrical insulation and moisture resistance properties. For example, synthetic resins having a low dielectric constant, a high solubility and a low moisture uptake as well as a high glass transition temperature (Tg) can be desirable combination of properties for electrical applications.

The use of synthetic resins in electronic applications can also influence the electrical signals generated in the electronics. Increases in electrical signal frequency in an electronic system (e.g., a computer system) allows for data to be processed at a higher rate. Synthetic resins in the vicinity of such electrical signals, however, can exert a large influence on transmission loss of such electrical signals in a high frequency circuit. To minimize this influence, synthetic resins having a low dielectric constant and a low dissipation factor, in addition to the other properties discussed above, are desired.

Synthetic resins, however, can be flammable. As such, different approaches have been made to impart flame resistance to synthetic resins. Two main approaches have been taken to providing flame resistance. The first is a "Green" approach in which halogen-free compounds are used. The second approach makes use of halogen compounds. Halogenated compounds have been used for decades in the electronic industry to impart flame resistance to electrical and electronic assemblies. For example, tetrabromobisphenol-A (TBBA) has been a workhorse flame resistance in electrical laminates for many years. Halogenated compounds, however, are now being scrutinized by environmental groups due to the possibility of dioxin formation during the incineration of electronic components at their end of life. In many developed countries the burning of the components is regulated and controlled, however, in developing countries, burning is often unregulated, increasing the likelihood of brominated dioxin release into the atmosphere.

SUMMARY

Embodiments of the present disclosure provide a thermosetting monomer comprising at least two of an aryl-cyanato group and at least two of a phosphorus group. For the various embodiments, such a thermosetting monomer can be represented by a compound of Formula (I):

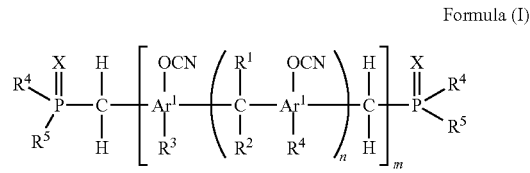

Formula (I)

wherein m is an integer from 1 to 20; wherein n is an integer from 0 to 20 with the proviso that when n is 0 then m is an integer from 2 to 20; wherein X is selected from the group consisting of sulfur, oxygen, a lone electron pair, and combinations thereof; wherein each $R^1$ and $R^2$ is independently a hydrogen, an aliphatic moiety having 1 to 20 carbon atoms, an aromatic hydrocarbon moiety having 6 to 20 carbon atoms, where the aliphatic moiety and the aromatic hydrocarbon moiety can be joined to form a cyclic structure; wherein $R^3$ is selected from the group consisting of a hydrogen, an aliphatic moiety having 1 to 20 carbon atoms, an aromatic hydrocarbon moiety having 6 to 20 carbon atoms, $R^4R^5P(=X)CH_2$—, and $ROCH_2$—, where R is an aliphatic moiety having 1 to 20 carbon atoms; wherein each $R^4$ and $R^5$ is independently an aliphatic moiety having 1 to 20 carbon atoms, an aromatic hydrocarbon moiety having 6 to 20 carbon atoms, where the aliphatic moiety and the aromatic hydrocarbon moiety can be joined to form a cyclic structure, RX—, or wherein $R^4$ and $R^5$ together are $Ar^2X$—; and wherein each $Ar^1$ and $Ar^2$ is independently a benzene, a naphthalene, of a biphenyl.

The various embodiments also include a composition that includes the thermosetting monomer of the present disclosure. For the various embodiments, the composition having the thermosetting monomer can be used to prepare a resin sheet, a resin clad metal foil, a prepreg, a laminated board, or a multi-layer board, among other items. In an additional embodiment, the composition having the thermosetting monomer of the present disclosure can further include a resin, such as a bismaleimide-triazine epoxy resin or FR5 epoxy resin, where the thermosetting monomer of the present disclosure and the resin can be used to prepare the aforementioned items.

For the various embodiments, a process for making the thermosetting monomer can include First formation of a phosphorus-substituted polyphenol by condensing an active phosphorous compound (H—P(.dbd.X)R.sup.4R.sup.5) with and an etherified resole followed by conversion to a polycyanate with cyanogen halide and a base. In the case where the etherified resole is butyl ether bisphenol-A resole and the active phosphorus compound is H-DOP (9,10-dihydro-9-oxa-10-phosphaphenanthrene-10-oxide), the phosphorus substituted polyphenol will be called DOP-BN and the polycyanate will be called DOP-BN polycyanate.

DETAILED DESCRIPTION

Figure 1:
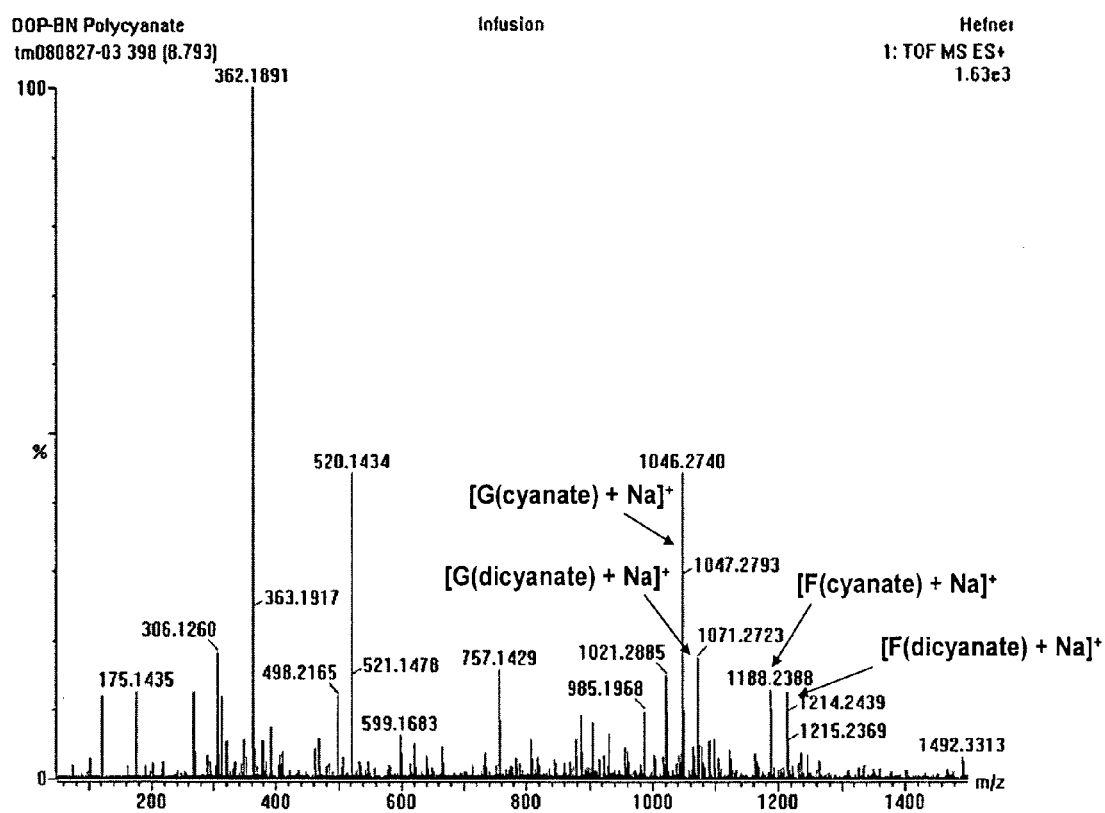
FIG. 1 provides a positive electrospray ionization mass spectrum from DOP-BN polycyanate Sample of the present disclosure.

Embodiments of the present disclosure include a thermosetting monomer that includes at least two of an aryl-cyanato group and at least two of a phosphorus group. For the various embodiments, the thermosetting monomer can be a cyanate derivative of a phosphorus-substituted polyphenol formed by condensing an active phosphorous compound (H—P(=X)R$^4$R$^5$) with and an etherified resole. In the particular case where the etherified resole is from bisphenol A and the active phosphorus compound is H-DOP (9,10-dihydro-9-oxa-10-phosphaphenanthrene-10-oxide) the phosphorus substituted polyphenol will be called DOP-BN and the polycyanate will be called DOP-BN polycyanate. The thermosetting monomer of the present disclosure is then obtainable from the reaction of the DOP-BN and a compound such as a cyanogen halide (e.g., cyanogen bromide) that reacts with a hydroxy group on the DOP-BN to yield a cyanato group.

For the various embodiments, the thermosetting monomer of the present disclosure can be used as, among other things, a self-curing compound and/or as a component in a hardener composition for a curable composition. The thermosetting monomer of the present disclosure can also be used as a reactive starting material for reacting with other polymers. For example, the aryl-cyanato group of the thermosetting monomer may be reacted with epoxy resins. In this embodiment, the thermosetting monomer acts as a crosslinking agent, curing agent and/or a hardener for the epoxy resin.

The thermosetting monomer of the present disclosure also provide the advantage of being halogen free while acting as a flame retardant for cured compositions formed with at least a portion of the thermosetting monomer. Such cured compositions that include the thermosetting monomer can also have suitable thermal and electrical properties useful as protective films, adhesive materials and/or insulating materials in a variety of electronic applications.

Specifically, the thermosetting monomer of the present disclosure can provide improvements in thermomechanical properties, such as improvements in glass transition temperature of a cured polymer of the thermosetting monomer and a bismaleimide-triazine (BT)-epoxy resin as compared to the cured polymer of DOP-BN and the BT-epoxy resin. In addition, formulations containing the thermosetting monomer of the present disclosure exhibited significantly improved viscosity stability over ones containing DOP-BN. The curable compositions of the present disclosure may also provide, in addition to flame resistance, other desired physical properties, such as dielectric characteristics, heat resistance, and processability (including solvent solubility).

For the various embodiments, the thermosetting monomer of the present disclosure includes at least two of an aryl-cyanato group and at least two of a phosphorus group. As used herein, the aryl-cyanato group can be a mono- or polycyclic aromatic hydrocarbon group that include at least one cyanato group (—OCN) attached thereto. In addition, the phosphorus group can also be a mono- or polycyclic aromatic hydrocarbon group that includes at least a phosphorous atom attached thereto.

For the various embodiments, such a thermosetting monomer can be represented by a compound of Formula (I):

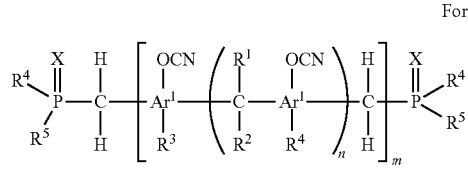

Formula (I)

wherein m is an integer from 1 to 20; wherein n is an integer from 0 to 20 with the proviso that when n is 0 then m is an integer from 2 to 20; wherein X is selected from the group consisting of sulfur, oxygen, a lone electron pair, and combinations thereof; wherein each R$^1$ and R$^2$ is independently a hydrogen, an aliphatic moiety having 1 to 20 carbon atoms, an aromatic hydrocarbon moiety having 6 to 20 carbon atoms, where the aliphatic moiety and the aromatic hydrocarbon moiety can be joined to form a cyclic structure; wherein R$^3$ is selected from the group consisting of a hydrogen, an aliphatic moiety having 1 to 20 carbon atoms, an aromatic hydrocarbon moiety having 6 to 20 carbon atoms, R$^4$R$^5$P(=X)CH$_2$—, and ROCH$_2$—, where R is an aliphatic moiety having 1 to 20 carbon atoms; and wherein each R$^4$ and R$^5$ is independently an aliphatic moiety having 1 to 20 carbon atoms, an aromatic hydrocarbon moiety having 6 to 20 carbon atoms, where the aliphatic moiety and the aromatic hydrocarbon moiety can be joined to form a cyclic structure, RX—, or wherein R$^4$ and R$^5$ together are Ar$^2$X—; and wherein each Ar$^1$ and Ar$^2$ is independently a benzene, a naphthalene, of a biphenyl.

As used herein, an aliphatic moiety includes saturated or unsaturated linear or branched hydrocarbon groups. This term is used to encompass, for example, alkyl, alkenyl, and alkynyl groups. As used herein, an aromatic hydrocarbon moiety includes mono- or polynuclear aromatic hydrocarbon groups.

Preferred thermosetting monomers of Formula (I) include those where X is oxygen, n is 1, m is 1, each R$^1$ and R$^2$ is a methyl group, R$^3$ is R$^4$R$^5$P(=X)CH$_2$—, and R$^4$ and R$^5$ together are Ar$^2$X, wherein Ar$^2$ is biphenyl such that R$^4$R$^5$P(=X)— is represented by a compound of Formula (II):

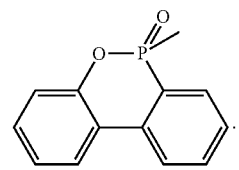

Formula (II)

Additional preferred thermosetting monomers of Formula (I) include those were X is oxygen, n is 0, m is 2 or 3, R$^3$ is R$^4$R$^5$P(=X)CH$_2$—, and R$^4$ and R$^5$ together are Ar$^2$X, wherein Ar$^2$ is biphenyl such that R$^4$R$^5$P(=X)— is represented by the compound of Formula (II). Additional preferred thermosetting monomers of Formula (I) are those in which R$^4$R$^5$P(=X)CH$_2$— is (C$_2$H$_5$O$_2$)$_2$P(=O)—, (PhO)$_2$P(=O)—, Ph(MeO)P(=O)— and Ph$_2$P(=O)—, where Ph is a phenyl group (C$_6$H$_5$—). Preferably, Ar$^1$ is benzene. Additional structures for R$^4$R$^5$P(=X)— include:

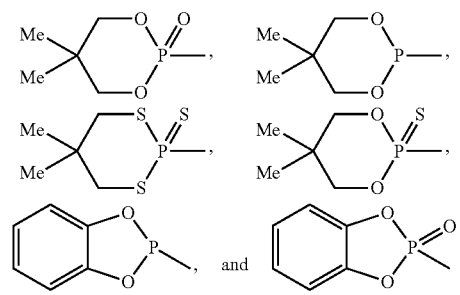

As used herein, the at least two of the phosphorus group for the thermosetting monomer can be derived from (9,10-dihydro-9-oxa-10-phosphaphenanthrene-10-oxide) (H-DOP).

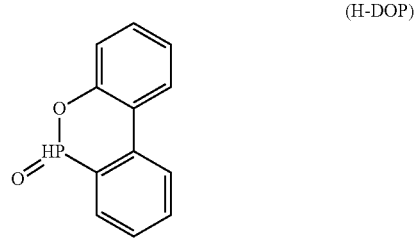
(H-DOP)

The H-DOP is commercially available under the Trade name "Sanko-HCA" from Sanko of Japan, or "Polydis® PD 3710", which is commercially available from Struktol® of Germany.

For the various embodiments, the H-DOP can be reacted with an etherified resole. Examples of suitable etherified resole include butyl ether bisphenol-A resoles, which are made with bisphenol A, formaldehyde and n-butanol. The etherified resole are typically a mixture of monomeric, dimeric and oligomeric structures. Examples of commercially available etherified resoles include SANTOLINK™ EP 560, which is a butyl etherified phenol formaldehyde condensation product and PHENODUR™ VPR 1785/50, which is a butoxymethylated phenol novolac, which the manufacturer characterizes as a highly butyl etherified resole based on a cresol mixture with a weight average molecular weight from 4000 to 6000 and a polydispersity from 2 to 3. Both of these products are available from UCB Group, a company headquartered in Brussels, Belgium, and its affiliate, UCB GmbH & Co. KG, a company incorporated in Germany. Other resole compounds available from UCB include for example PHENODUR™ PR 401, PHENODUR™ PR 411, PHENODUR™ PR 515, PHENODUR™ PR 711, PHENODUR™ PR 612, PHENODUR™ PR 722, PHENODUR™ PR 733, PHENODUR™ PR 565, and PHENODUR™ VPR 1775.

An example of the butyl ether bisphenol-A resole is shown below:

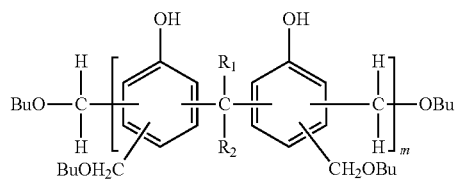

where Bu is a butyl group and m can be an integer of 1 to about 10. As discussed herein, the butyl ether bisphenol-A resole may be present as a combination of monomers, dimers and/or oligomers of the butyl ether bisphenol-A resole. In addition, one or more of the butyl ether groups (—$CH_2$OBu) in the ortho positions in the butyl ether bisphenol-A resole can be replaced with other groups, such as —H, and —$CH_2$OH. The above structure is a simplification of the actual structure. As is well known in the art, some of the bridging groups can be —$CH_2OCH_2$— rather than methylene bridges. This can be controlled by the process parameters used to make the resole (catalyst type, pH, alcohol concentration, and temperature among others).

For the various embodiments, the active phosphorous compound (such as H-DOP) can be reacted with the etherified resole by blending or mixing them together to form a reactive composition. The reactive composition can be heated to initiate the reaction of the two components to form an alcohol and form the phosphorus polyphenol intermediate. For the various embodiments, the reaction temperature is preferably below the decomposition temperature of the starting materials. Generally, the reaction temperature is greater than 100 degrees Celsius (° C.), preferably greater than 120° C., and more preferably greater than 150° C. The reaction is preferably carried out for a period of time sufficient to a react the H-P-moieties of the H-DOP with the —OBu moieties of the butyl ether bisphenol-A resole. The time of reaction is typically from 60 minutes to 12 hours, preferably from 2 hours to 6 hours, and more preferably from 2 hours to 4 hours.

For the various embodiments, the reaction is preferably carried out without the presence of water (generally the water is present in less than 5 weight percent (wt. %), more preferable less than 3 wt. % percent and most preferable less than 1 wt. %) because water may tend to react with the H-DOP. Removal of the alcohol co-product generally helps drive the reaction to completion. The pressure in the reaction vessel is therefore preferably reduced to a pressure below atmospheric pressure, such as a pressure of 0.1 bar or less, to help drive off the alcohol or byproducts at a temperature below the abovementioned lowest decomposition temperature. The reaction vessel may optionally be purged with a gas or volatile organic liquid to further assist in removing byproduct(s). The gas or volatile organic liquid is preferably inert to the contents of the reaction vessel. An example of such an inert gas includes, but is not limited to, nitrogen gas.

The butyl ether bisphenol-A resole is usually dissolved in an organic solvent, such as butanol, xylene, or Dowanol™ PM (The Dow Chemical Company); and part of the solvent can be removed either by heat or applying vacuum to the solution before the addition of H-DOP. The H-DOP and the etherified resole are preferably combined at a weight ratio (H-DOP:etherified resole) in the range from 10:1 to 1:10, preferably from 5:1 to 1:5, more preferably from 2:1 to 1:2, most preferably in the range from 1.1:1 to 1:1.1 based on total solids content of the composition. If desired, other materials such as catalysts or solvents may be added to the reaction mixture of the H-DOP and the etherified resole.

For the various embodiments, the reaction products of the H-DOP and the butyl ether bisphenol-A resole displaces most, but not necessarily all, of the butyl ether groups present on the butyl ether bisphenol-A resole. The resulting compounds, referred to herein as DOP-BN, are shown below.

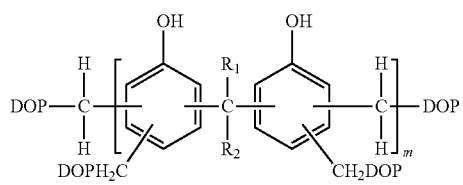

Generally, the DOP-BN reaction products from the reaction of H-DOP and the etherified resole is a mixture of oligomers (m=1 through 20). The number average degree of polymerization of the phosphorus polyphenol product is related to the molecular weight of the etherified resole starting material.

For the various embodiments, the thermosetting monomers of Formula (I) provided herein can be prepared by reacting DOP-BN with a compound that will react with a hydroxy group to yield a cyanato group. Examples of such compounds include cyanogen halides, such as cyanogen bromide and cyanogen chloride. The reaction is conducted in the presence of a base that can include alkali metal hydroxides and/or aliphatic amines, such as triethylamine and/or sodium hydroxide.

For the various embodiments, the reaction can be conducted at a low temperature in view of the exothermic nature of the reaction and the volatility of the cyanogen halide. For example, the reaction temperature can be from −40° C. to 40° C., preferably −20° C. to 10° C. The use of inert organic solvents is possible, where such inert organic solvents include, but are not limited to, aromatic hydrocarbons, such as benzenes, toluene or xylene; ethers, such as diethyl ether or tetrahydrofuran; halogenated aliphatic or aromatic hydrocarbons, such as methylene chloride or chlorobenzene; alcohols such as methanol, ethanol, or isopropyl alcohol; and/or ketones, such as acetone, methyl ethyl ketone or methyl isobutyl ketone.

The thermosetting monomer of the present disclosure can have a phosphorus content of at least 0.1 weight percent (wt. %) to 3.5 wt. %. In an additional embodiment, the thermosetting monomer of the present disclosure can have a phosphorus content of greater than 3.5 wt. %, such as at least 6 wt. %, which can make it useful in the preparation of flame resistant materials. For example, it is possible that the phosphorus content of the reaction products can be from 4 to 12 percent, from 5 to 9 or from 6 to 8 weight percent. The embodiments of the present disclosure can also be useful in other applications requiring flame resistant materials, including semiconductor packaging applications, electrical and electronic applications, and composite applications. In addition, the thermosetting monomer is substantially free of both bromine atoms and of halogen atoms.

Di and polycyanates are notoriously difficult to cure, requiring high temperatures and catalysts which can interfere with many end uses, such as metal containing catalysts which interfere with use in laminates, coatings, encapsulants, adhesives and potting compounds for electronics. The thermosetting monomer of the present disclosure, however, revealed remarkable improvement in the uncatalyzed cure profile (cyclotrimerization) relative to conventional dicyanates, specifically bisphenol A dicyanate (BPA DCN). For example, onset to cure for an example of the thermosetting monomer of the present disclosure was 180.2° C. versus 305.1° C. for dicyanate of bisphenol A (BPA DCN). Cure enthalpy for the cure of this example of the thermosetting monomer was 232.1 joules/gram versus 550.2 joules/gram for BPA DCN. As appreciated, this lower enthalpy can provide for more controlled curing and the reduction of thermally damaged parts. Another improvement was that the thermosetting monomers of the present disclosure gave a full cure versus BPA DCN, which exhibited additional cure energy commencing at 265.8° C. These beneficial properties were also evident in a blend prepared using the thermosetting monomer of the present disclosure and BPA DCN, as well as in blends of the thermosetting monomer of the present disclosure and bismaleimide of 4,4'-diaminodiphenylmethane.

For the various embodiments, the composition of the thermosetting monomer of the present disclosure can undergo self thermal polymerization (e.g., homopolymerization). The self thermal polymerization of the thermosetting monomer can involve trimerization of the cyanato groups of Formula (I) to form a cyanate that has a three-dimensional network structure. Generally, the polymerization or curing of cyanates in the thermosetting monomer of Formula (I), in accordance with the disclosure, can be carried out by first melting the thermosetting monomer to obtain a homogeneous melt. For some applications, such as preparation of prepreg used for electrical laminates and other composite applications, is it useful to dissolve the polycyanate in a suitable solvent. Examples of suitable solvents include, but are not limited to, alcohols such as Dowanol™ PMA (The Dow Chemical Company), ketones such as acetone and/or methyl ethyl ketone, esters, and/or aromatic hydrocarbons.

The homopolymerization can be carried out at lower temperatures with the aid of a cyanate polymerization catalyst. Examples of such cyanate polymerization catalysts can include Lewis acids, such as aluminium chloride, boron trifluoride, ferric chloride, titanium chloride, and zinc chloride; protonic acids, such as hydrochloric and other mineral acids; salts of weak acids, such as sodium acetate, sodium cyanide, sodium cyanate, potassium thiocyanate, sodium bicarbonate, sodium boronate, and phenylmercuric acetate; bases, such as sodium methoxide, sodium hydroxide, pyridine, triethylamine; and non-ionic coordination compounds, such as cobalt, iron, zinc, and copper acetylacetonates. The amount of the cyanate polymerization catalyst used can vary, and generally will be 0.05 to 5 mole percent, preferably 0.05 to 0.5 mole percent.

Embodiments of the present disclosure also provide for a composition that includes the thermosetting monomer of the present disclosure and at least one of a formulation component. For the various embodiments, the formulation component of the composition can either be reactive or non-reactive with the thermosetting monomer of the present disclosure. For the various embodiments, compositions that include the thermosetting monomer and the formulation component can be obtained by reacting, blending or mixing the thermosetting monomer of the present disclosure with the at least one formulation component. Examples of such formulation components include, but are not limited to, epoxy resins, polyepoxide resins, cyanate esters, dicyanate esters, polycyanate esters, cyanate aromatic esters, maleimide resins, thermoplastic polymers, thermoplastic resins, polyurethanes, polyisocyanates, benzoxazine ring-containing compounds, unsaturated resin systems containing double or triple bonds, and combinations thereof.

For the various embodiments, examples of the thermosetting resin useful in forming the composition with the thermosetting monomers of the present disclosure may include at least one epoxy resin and/or polyepoxide resin, where combinations of one or more of the epoxy resins and one or more of the polyepoxide resins are possible. Examples of such epoxy resins include, but are not limited to, those selected from halogen-free epoxies, phosphorus-free epoxies, brominated epoxies, and phosphorus-containing epoxies and mixtures thereof, epoxy functional polyoxazolidone containing compounds, cycloaliphatic epoxies, GMA/styrene copolymers, and the reaction product of liquid epoxy resins (LER) and tetrabromobisphenol A (TBBA) resins.

Additional epoxy compounds include bismaleimide-triazine resins (BT-resins), mixtures of epoxy resins and BT-resins (BT-epoxy), epoxy novolac resins, cresole epoxy novolacs, trisepoxy compounds, epoxidized bisphenol A novolacs, dicyclopentadiene phenol epoxy novolacs, glycidyl ethers of: tetraphenolethane, resorcinol, catechol, bisphenol, bisphenol-A, bisphenol AP (1,1-bis(4-hydroxylphenyl)-1-phenyl ethane), bisphenol F, bisphenol K, tetrabromobisphenol A, phenol-formaldehyde novolac resins, hydroquinone, alkyl substituted phenol-formaldehyde resins, phenol-hydroxybenzaldehyde resins, cresol-hydroxybenzaldehyde resins, dicyclopentadiene-phenol resins, dicyclopentadiene-substituted phenol resins tetramethylbiphenol, tetramethyltetrabromobiphenol, tetramethyltribromobiphenol, tetrachlorobisphenol A, and combinations thereof.

Examples of polyepoxide resins include, but are not limited to, those described in U.S. Pat. No. 6,645,631. The polyepoxide resins disclosed in U.S. Pat. No. 6,645,631 are the reaction products of an epoxy compound containing at least two epoxy groups and a reactive phosphorus-containing compound such as 3,4,5,6-dibenzo-1,2-oxaphosphane-2-oxide (DOP), or 10-(2'5'-dihydroxyphenyl)-9,10-dihydro-9-oxa-10-phosphaphenanthrene-10-oxide (DOP-HQ).

A Lewis acid may also be employed in the compositions that include an epoxy resin. The Lewis acid may include, for example, one or a mixture of two or more halides, oxides, hydroxides and alkoxides of zinc, tin, titanium, cobalt, manganese, iron, silicon, aluminum, and boron. Examples of such Lewis acids, and anhydrides of Lewis acids include boric acid, metaboric acid, optionally substituted boroxines (such as trimethoxy boroxine, trimethyl boroxine or triethyl boroxine), optionally substituted oxides of boron, alkyl borates, boron halides, zinc halides (such as zinc chloride) and other Lewis acids that tend to have a relatively weak conjugate base.

It is also within the scope of this disclosure to copolymerize the thermosetting monomers with one or more cyanate esters, dicyanate esters and/or cyanate aromatic esters. The amount of such cyanate esters which can be copolymerized with the thermosetting monomers of this disclosure can vary and generally will be dictated by the particular properties desired to be imparted to the resulting copolymers. For example, the degree of crosslinking of the copolymer can be increased in some instances by incorporating such aromatic short chain (di)cyanates.

Embodiments of the present disclosure can also include the use of at least one maleimide resin with the thermosetting monomers of the present disclosure. Examples of suitable maleimide resins include, but are not limited to, those having two maleimide groups derived from maleic anhydride and diamines or polyamines. Suitable maleimide resins include bismaleimides such as 4,4'-diaminodiphenylmethane, among others.

Embodiments of the present disclosure also provide for a composition that includes the thermosetting monomer of the present disclosure and at least one thermoplastic polymer. Typical thermoplastic polymers include, but are not limited to, polymers produced from vinyl aromatic monomers and hydrogenated versions thereof, including both diene and aromatic hydrogenated versions, including aromatic hydrogenation, such as styrene-butadiene block copolymers, polystyrene (including high impact polystyrene), acrylonitrile-butadiene-styrene (ABS) copolymers, and styrene-acrylonitrile copolymers (SAN); polycarbonate (PC), ABS/PC compositions, polyethylene, polyethylene terephthalate, polypropylene, polyphenylenoxides (PPO), hydroxy phenoxy ether polymers (PHE), ethylene vinyl alcohol copolymers, ethylene acrylic acid copolymers, polyolefin carbon monoxide interpolymers, chlorinated polyethylene, polyphenylene ether, polyolefins, olefin copolymers, cyclic olefin copolymers, and combinations or blends thereof.

In an additional embodiment, the composition of the present disclosure can include the thermosetting monomer of the present disclosure and at least one reactive and/or non-reactive thermoplastic resin. Examples of such thermoplastic resins include, but are not limited to, polyphenylsulfones, polysulfones, polyethersulfones, polyvinylidene fluoride, polyetherimide, polypthalimide, polybenzimidiazole, acyrlics, phenoxy, and combinations or blends thereof.

For the various embodiments, the thermosetting monomer of the present disclosure can be blended with the thermoplastic resin to form a hybrid crosslink network. Preparation of the compositions of the present disclosure can be accomplished by suitable mixing means known in the art, including dry blending the individual components and subsequently melt mixing, either directly in the extruder used to make the finished article or pre-mixing in a separate extruder. Dry blends of the compositions can also be directly injection molded without pre-melt mixing.

When softened or melted by the application of heat, the composition of the thermosetting monomers of the present disclosure and the thermoplastic resin can be formed or molded using conventional techniques such as compression molding, injection molding, gas assisted injection molding, calendaring, vacuum forming, thermoforming, extrusion and/or blow molding, alone or in combination. The composition of the thermosetting monomers of the present disclosure and the thermoplastic resin may also be formed, spun, or drawn into films, fibers, multi-layer laminates or extruded sheets, or can be compounded with one or more organic or inorganic substances.

Embodiments of the present disclosure also provide for a composition that includes the thermosetting monomer of the present disclosure and at least one of a polyurethane, a polyisocyanate, a benzoxazine ring-containing compound, an unsaturated resin system containing double or triple bonds, and combinations thereof.

The compositions of the present disclosure described above may also optionally make use of at least one catalyst. Examples of suitable curing catalysts include amines, dicyandiamides, substituted guanidines, phenolics, amino, benzoxazines, anhydrides, amido amines, polyamides, phosphines, ammonium, phosphonium, arsonium, sulfonium moieties or mixtures thereof.

Because of their unique combination of properties, the thermosetting monomer and/or compositions that include the thermosetting monomer may be useful in the preparation of various articles of manufacture. Thus, the disclosure also includes prepregs of the above composition as well as shaped articles, reinforced compositions, laminates, electrical laminates, coating, molded articles, adhesives, composite products as hereinafter described from cured or partially cured thermosetting monomer or compositions that include the thermosetting monomer of the disclosure. In addition, the compositions of the disclosure can be used for various purposes in the form of a dried powder, pellets, a homogeneous mass, impregnated products or/and compounds.

A variety of additional additives may be added to the composition of the present disclosure. Examples of these additional additives include fibrous reinforcement, fillers, pigments, dyestuffs, thickening agents, wetting agents, lubricants, flame-retardants and the like. Suitable fibrous and/or particulate reinforcing materials include silica, alumina trihydrate, aluminum oxide, aluminum hydroxide oxide, metal oxides, nanotubes, glass fibers, quartz fibers, carbon fibers, boron fibers, Kevlar fibers and Teflon fibers, among others. A size range for the fibrous and/or particulate reinforcing materials can include 0.5 nm to 100 μm. For the various embodiments, the fibrous reinforcing materials can come in the form of a mat, cloth or continuous fibers.

The fibrous or reinforcing material is present in the composition in an amount effective to impart increased strength to the composition for the intended purpose, generally from 10 to 70 wt. %, usually from 30 to 65 wt. %, based on the weight of the total composition. The laminates of the disclosure can optionally include one or more layers of a different material and in electrical laminates this can include one or more layers of a conductive material such as copper or the like. When the resin composition of this disclosure is used for producing molded articles, laminated articles or bonded structures, the curing is desirably effected under pressure.

In a partially cured state, the fibrous reinforcement impregnated with the composition of the present disclosure can be subjected to a relatively mild heat treatment ("B-staged ") to form a "prepreg." The prepreg can then subjected to elevated temperature and pressure so as to more completely cure the composition to a hard, inflexible state. A plurality of prepregs can be layered and cured to form a laminate having utility in circuit boards.

Embodiments of the compositions may also include at least one of a synergist to help improve the flame out ability of the cured composition. Examples of such synergists include, but are not limited to, magnesium hydroxide, zinc borate, metalocenes and combinations there. In addition, embodiments of the compositions may also include adhesion promoters, such as modified organosilanes (epoxidized, methacryl, amino), acetylacetonates, sulfur containing molecules and combinations thereof. Other additives can include, but are not limited to, wetting and dispersing aids such as modified organosilanes, Byk® 900 series and W 9010 (Byk-Chemie GmbH), modified fluorocarbons and combinations thereof; air release additives such as Byk® A530, Byk® A525, Byk® A555, and Byk® A 560 (Byk-Chemie GmbH); surface modifiers such as slip and gloss additives; mold release agents such as waxes; and other functional additives or prereacted products to improve polymer properties such as isocyanates, isocyanurates, cyanate esters, allyl containing molecules or other ethylenically unsaturated compounds, acrylates and combinations thereof.

For the various embodiments, a resin sheet can be formed from the thermosetting monomer and/or compositions of the present disclosure. In one embodiment, a plurality of sheets can be bonded together to form a laminated board, where the sheets comprise at least one of the resin sheet. The thermosetting monomer and/or compositions that include the thermosetting monomer can also be used to form a resin clad metal foil. For example, a metal foil, such as a copper foil, can be coated with the thermosetting monomer and/or compositions that include the thermosetting monomer of the present disclosure. The various embodiments also include a multilayer board that can be prepared by coating a laminated substrate with the thermosetting monomer and/or compositions of the present disclosure.

The thermosetting monomers of this disclosure comprise one or more components which can each be used in any desired form such as solid, solution or dispersion. These components are mixed in solvent or in the absence of a solvent to form the compositions of this disclosure. For example, the mixing procedure comprises mixing solutions of the thermosetting monomers and one or more of the formulation components or either separately or together in a suitable inert organic solvent, such as for example, ketones such as methyl ethyl ketone, chlorinated hydrocarbons such as methylene chloride, ethers and the like, and homogenizing the resulting mixed solution at room temperature or at an elevated temperature below the boiling point of the solvents to form a composition in the form of a solution. When homogenizing these solutions at room temperature or at an elevated temperature, some reactions may take place between the constituent elements. So long as the resins components are maintained in the state of solution without gelation, such reactions do not particularly affect the operability of the resulting composition in, for example, a bonding, coating, laminating or molding operation.

For the various embodiments, the thermosetting monomer and/or compositions of the present disclosure can applied to a substrate as a coating or adhesive layer. Alternatively, the thermosetting monomer and/or compositions of the present disclosure can be molded or laminated in the form of powder, pellet or as impregnated in a substrate such as a fibrous reinforcement. The thermosetting monomer and/or compositions of the present disclosure can then be cured by the application of heat.

The heat necessary to provide the proper curing conditions can depend on the proportion of components constituting the composition and the nature of the components employed. In general, the composition of this disclosure may be cured by heating it at a temperature within the range of 0° C. to 300° C., preferably 100° C. to 250° C., although differing according to the presence of a catalyst or curing agent or its amount, or the types of the components in the composition. The time required for heating can be 30 seconds to 10 hours, where the exact time will differ according to whether the resin composition is used as a thin coating or as molded articles of relatively large thickness or as laminates or as matrix resins for fiber reinforced composites, particularly for electrical and electronic applications, e.g., when applied to an electrically nonconductive material and subsequently curing the composition.

EXAMPLES

The following examples are given to illustrate, but not limit, the scope of this invention.

Materials

Tetrahydrofuran; (available from Sigma-Aldrich, hereinafter "Aldrich").

Anhydrous dichloromethane, (available from Aldrich).

9,10-dihydro-9-oxa-l0-phosphaphenanthrene-10-oxide (H-DOP, "Sanko-HCA," which is commercially available from Sanko of Japan).

Butyl ether bisphenol-A resole (SANTOLINK™ EP 560, an etherified resoles commercially available from UCB GmbH & Co.).

Nitrogen, (available from Air Products).

Cyanogen bromide, (available from Aldrich).

Triethylamine, (base, available from Aldrich).

Dichloromethane, (available from Aldrich).

Granular anhydrous sodium sulfate, (available from Aldrich).

Bisphenol A dicyanate, (available from Lonza Group, Switzerland).

4,4'-bis(maleimido)diphenylmethane, (commercial grade, Compimide MDAB, Evonik Degussa GmbH).

D.E.N.™ 438, (Epoxy Novolak Resin, The Dow Chemical Company).

N-phenylmaleimide (available from Aldrich).

Primaset™ BA-230s (a partially trimerized bisphenol A cyanate ester, Lonza Group Limited, Switzerland).

2-butanone (methylethylketone solvent, available from The Dow Chemical Company).

n-Butanol (available from Aldrich).

Dowanol™ PM (propylene glycol methyl ether, The Dow Chemical Company).

Zn Hexanoate (OMG Kokkola Chemicals, Finland).

Example 1

Synthesis of Solid DOP-BN

To a 3 liter, three neck flask preheated to 130° C. equipped with a nitrogen inlet, condenser, mechanical stirrer, and a temperature controller was added 1420 g of D.E.N.™ 438 which had been preheated to 105° C. The stir speed was set at 75 rotations per minute (rpm) and the nitrogen flow set at 60 ml/min. Once the material in the flask reached 130° C., 308 g of 4,4' bis(maleimido)diphenylmethane, and 206 g of N-phenylmaleimide were added to the reactor. After the temperature stabilized at 130° C., the blend was mixed for 45 minutes. After 45 minutes, the heating lamps were removed and 404 g of 2-butanone was added to reactor drop-wise via an addition funnel. After the addition of the 2-butanone, the temperature controller was set at 60° C. and the solution blended with the stir blade set at 75 rpm for 30 minutes. The resulting solution is referred to herein as Masterblend A.

To prepare the solid DOP-BN, a 60 g sample of Masterblend A was placed it in a 32 ounce, wide-mouth, glass jar and then into a vacuum oven set at 100° C. for 18 hours to remove the solvents. The resultant solid material exhibited a fluffy, crystalline appearance. A 2.661 mg sample was analyzed via thermogravimetric analysis on a TA Instruments, Q50 TGA under a 50 cc/minute nitrogen purge according to the following procedure: Ramp from room temperature to 171° C. at 20° C./minute, Isotherm at 171° C. for 45 minutes. The total weight loss was measured at 2.8%.

High pressure liquid chromatographic (HPLC) analysis (UV detection at 254 and 305 nm with diode array, Prontosil 120-3-$C_{18}$-ace-EPS 3.0 um, 150×4.6 mm column, acetonitrile/water eluent (50/50 start with a gradient to 100% acetonitrile, 40° C., 1.0 mL/min flow rate) of Masterblend A (the DOP-BN) revealed 21 components with 3 predominant components comprising 31.22 area %, 27.11 area % and 11.05 area %. Fourier transform infrared spectrophotometric (FTIR) analysis (Nicolet FT-IR Spectrometer) of a potassium bromide pellet of the DOP-BN revealed hydroxyl group absorbance at 3212.8 cm$^{-1}$ and a sharp strong aromatic band absorbance at 1431.0 cm$^{-1}$ due to phenyl ring directly attached to the phosphorus atom.

Analysis of DOP-BN by Electrospray Ionization Liquid Chromatography Mass Spectrometry Solid DOP-BN samples were dissolved into tetrahydrofuran (approximately 10% v/v) and five (5) microliter aliquots of these solutions were analyzed by liquid chromatography electrospray ionisation mass spectrometry (ESI/LC/MS) on a Waters Alliance 2690 ternary gradient liquid chromatography system coupled to a Micromass QToF2, SN #UC-175, quadrupole/time of flight MS/MS system via a Micromass Z-spray electrospray (ESI) interface operating in the positive ion (PI) and negative ion (NI) modes. The following analysis conditions were used:

Column: 150×4.6 mm ID×5 μm, Zorbax SB-C3.
Mobile phase: A=DI Water w/0.05% Formic Acid and B=Tetrahydrofuran.
Gradient Program: 80/20 v/v A/B hold 1 minute, to 5/95 v/v A/B at 21 minutes Curve 6, hold 5 minutes, Total Run time=26 minutes.
Column temperature: 45° C.
Flow: 1.0 mL/min (split 2:1 away from interface).
UV detection: Diode Array 210 to 400 nm.
ESI conditions: Source Block: 110° C. Desolvation: 280° C.
Capillary: +/−2.5 kV.
Cone: +/−20 V.
MS conditions: MCP: 2150V Mode: +/−ions.
Scan: 50 to 4000 amu (+) Rate: 1.0 sec/scan
Scan: 50 to 3000 amu (−) Rate: 1.0 sec/scan
Lockspray Mass Calibrant=(PI/NI) 12.5 microgram/mL solution of DE-638 (Penoxsulam™, Chem. Abs. 219714-96-2, C16H14F5N5O5S) in methanol (M+H+=484.0714, M−H−=482.0558) at a flowrate of three (3) microliters per minute, one (1) scan acquired every five (5) seconds.

The ESI/LC/MS analysis provided the following proposed structures shown in Table 1, where only those components present at greater than 5 area % were considered.

TABLE 1

Assignments from ESI Analysis of the DOP-BN

| Area % | m/z Observed ESI/LC/MS | MW | Tentative Assignments |
|---|---|---|---|
| 45.1 (including a shoulder) | PI 1141.2604 (M + H)+, 1163.2454 (M + Na)+, NI 1139.2275 (M − H)−, | 1140 | 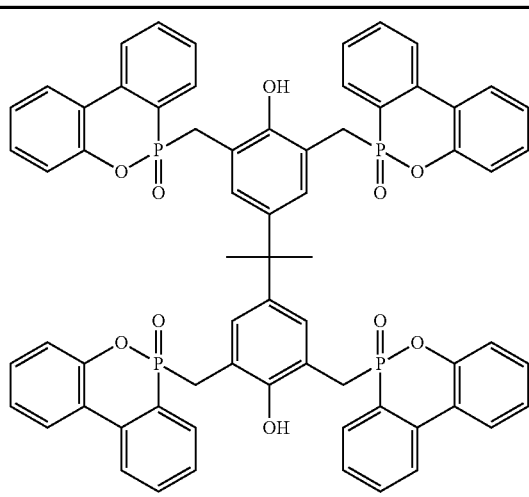 $C_{67}H_{52}O_{10}P_4$ 1140.251101 or isomer Error in Mass Measurement = 1.4 mDa at m/z 1141(+) |

TABLE 1-continued

Assignments from ESI Analysis of the DOP-BN

| Area % | m/z Observed ESI/LC/MS | MW | Tentative Assignments |
|---|---|---|---|
| 17.2 | PI 999.2999 (M + H)+, 1021.2844 (M + Na)+, NI 997.2697 (M − H)−, | 998 | $C_{59}H_{53}O_9P_3$ 998.290248 or isomer Error in Mass Measurement = 1.9 mDa at m/z 999(+) |
| 15.7 | PI 1837.4532 (M + H)+, 1859.4479 (M + Na)+, NI – | 1836 | $C_{109}H_{86}O_{16}P_6$ 1836.434167 or isomer Error in Mass Measurement = 11.3 mDa at m/z 1837(+) |

TABLE 1-continued

Assignments from ESI Analysis of the DOP-BN

| Area % | m/z Observed ESI/LC/MS | MW | Tentative Assignments |
|---|---|---|---|

Synthesis of the Polycyanate of DOP-BN

| 10.5 | PI 857.3348 (M + H)+, 879.3209 (M + Na)+, NI – And PI 1695.4910 (M + H)+, 1717.4763 (M + Na)+, NI – And PI 2533.6516 (M + H)+, 2555.6196 (M + Na)+, NI – | 856 And 1694 And 2532 (small) | $C_{51}H_{54}O_8P_2$ 856.329395 and $C_{101}H_{87}O_{15}P_5$ 1694.473314 plus |

TABLE 1-continued

Assignments from ESI Analysis of the DOP-BN

| Area % | m/z Observed ESI/LC/MS | MW | Tentative Assignments |
|---|---|---|---|

$C_{151}H_{120}O_{22}P_8$
2532.617233
Error in Mass Measurement = −2.4 mDa at m/z 857(+)
Error in Mass Measurement = 9.8 mDa at m/z 1695(+)
Error in Mass Measurement = 26.6 mDa at m/z 2533(+)

A 250 milliliter, three neck, glass, round bottom reactor was charged with the solid DOP-BN prepared as above (4.90 grams, 0.01 hydroxyl equivalent) and anhydrous dichloromethane (50 milliliters, 10.2 milliliter per gram of DOP-BN). The reactor was additionally equipped with a condenser (maintained at 0° C.), a thermometer, an overhead nitrogen inlet (1 liters per minute $N_2$ used), and magnetic stirring. The solution was stirred and its temperature was brought to 22° C.

Cyanogen bromide (1.134 grams, 0.0107 mole, 1.07:1 cyanogen bromide:hydroxyl equivalent ratio) was added to the solution and immediately dissolved therein. A dry ice-acetone bath for cooling was placed under the reactor followed cooling and equilibration of the stirred solution at −7° C. Triethylamine (1.03 grams, 0.0102 mole, 1.02 triethylamine:hydroxyl equivalent ratio) was added using a syringe in aliquots that maintained the reaction temperature at −7° C. to −3.5° C. The total addition time for the triethylamine was 12 minutes. Addition of the initial aliquot of triethylamine induced a light yellow color in the stirred solution which immediately turned colorless again. With further additions haziness indicative of triethylamine hydrobromide was observed. After 13 minutes of postreaction at −8° C. to −5° C. HPLC analysis (UV detection at 254 and 305 nm with diode array, Prontosil 120-3-$C_{18}$-ace-EPS 3.0 um, 150×4.6 mm column, acetonitrile/water eluent (50/50 start with a gradient to 100% acetonitrile, 40° C., 1.0 mL/min flow rate) of a sample of the reaction product revealed 31 components with every component present having a different retention time than those observed in the HPLC analysis of the DOP-BN. After a cumulative 32 minutes of postreaction at −8° C. to −5° C., the product slurry was added to a beaker of magnetically stirred deionized water (200 milliliters) and dichloromethane (50 milliliters) providing a mixture.

After 2 minutes of stirring, the mixture was added to a separatory funnel, allowed to settle, and then the dichloromethane layer recovered, with the aqueous layer discarded to waste. The dichloromethane solution was added back into the separatory funnel and extracted with fresh deionized water (100 milliliters) three additional times. The resultant hazy dichloromethane solution was dried over granular anhydrous sodium sulfate (5 grams) to give a clear solution which was then passed through a bed of anhydrous sodium sulfate (25 grams) supported on a 60 milliliter, medium fritted glass funnel attached to a side arm vacuum flask.

The clear, light yellow colored filtrate was rotary evaporated using a maximum oil bath temperature of 50° C. until the vacuum was <1 mm Hg. A total of 4.49 grams of white, crystalline product was recovered. FTIR analysis of a potassium bromide pellet of the polycyanate of DOP-BN revealed disappearance of the hydroxyl group absorbance, appearance of sharp strong cyanate group absorbance at 2253.7 and 2207.3 $cm^{-1}$, and maintenance of the sharp strong aromatic band absorbance at 1431.0 $cm^{-1}$ due to phenyl ring directly attached to the phosphorus atom.

HPLC/MS data indicate the conversion of the phenolic moieties into the desired cyanate ester functionality. FIG. 1 contains the positive ion ESI mass spectrum obtained by infusing a methanol solution of a sample of the polycyanate of DOP-BN. The major ions observed at masses 362.19 and 520.14 remain unidentified.

Figure 2:
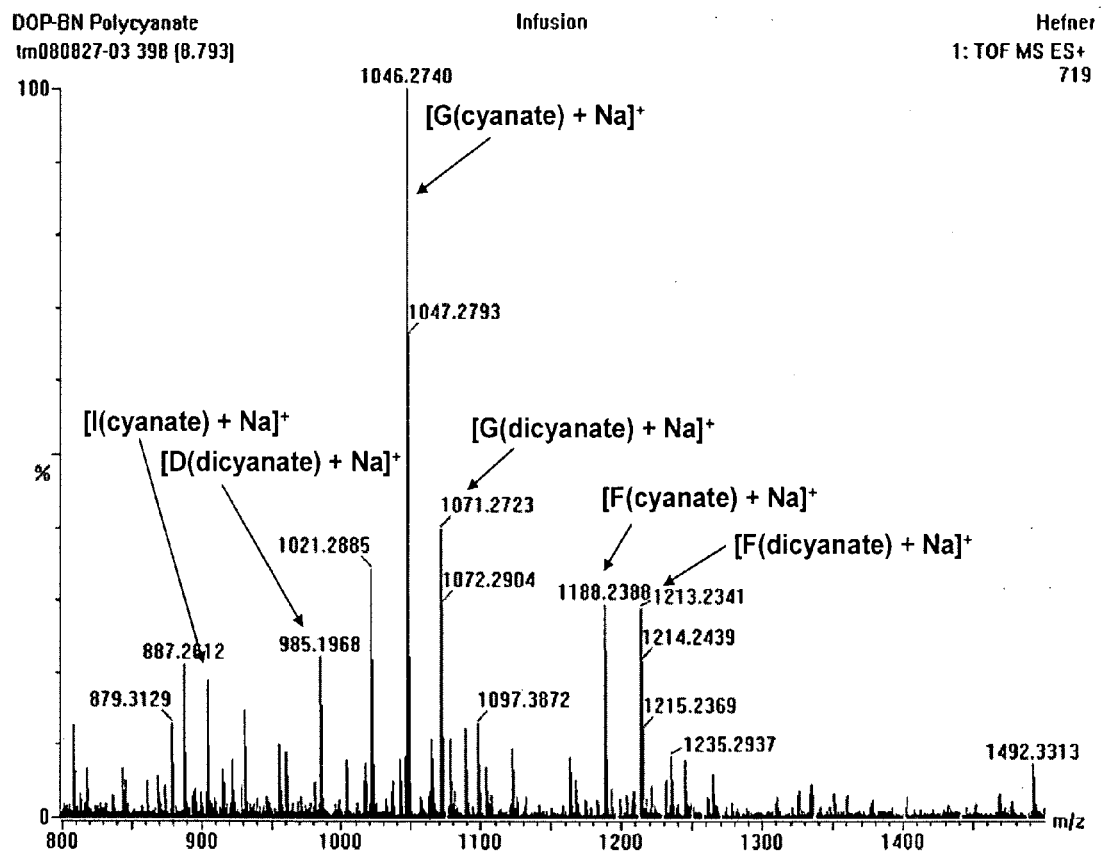
FIG. 2 provides an expanded positive electrospray ionization mass spectrum from DOP-BN polycyanate Sample of the present disclosure.

FIG. 2 focused on the higher mass range. The elemental compositions for a number of these ions can be assigned based on the accurate mass measurements determined for these ions. The ions identified are the cyanate analogs of the phenolic compounds observed in the DOP-BN starting material. Both mono- and dicyanates are observed and are shown in Table 2. Compound F(dicyanate) is the target compound for the polycyanate of DOP-BN sample.

TABLE 2

Assignments from ESI Analysis of the Polycyanate of DOP-BN

| Compound ID | m/z Obsrvd Pos Ion | Nom MW | Tentative Assignments |
|---|---|---|---|
| D(dicyanate) | 985.1968 (M + Na)⁺ | 962 | 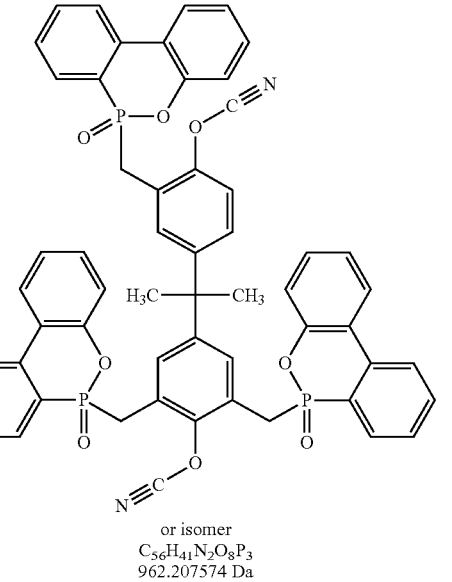<br>or isomer<br>$C_{56}H_{41}N_2O_8P_3$<br>962.207574 Da |
| E(cyanate) | 1188.2388 (M + Na)⁺ | 1165 | 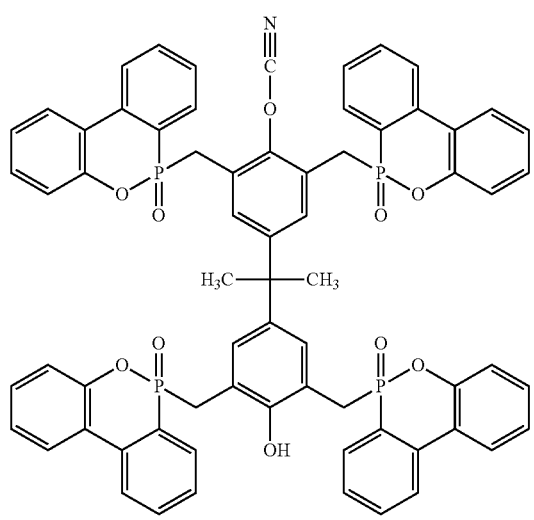 [SMILES: CC(C)(c1cc(CP2(=O)Oc3ccccc3-c3ccccc32)c(O)c(CP2(=O)Oc3ccccc3-c3ccccc32)c1)c1cc(CP2(=O)Oc3ccccc3-c3ccccc32)c(OC#N)c(CP2(=O)Oc3ccccc3-c3ccccc32)c1]<br>$C_{68}H_{51}NO_{10}P_4$ or isomer<br>1165.246341 Da |

TABLE 2-continued
Assignments from ESI Analysis of the Polycyanate of DOP-BN
| Compound ID | m/z Obsrvd Pos Ion | Nom MW | Tentative Assignments |
|---|---|---|---|
| F(dicyanate) | 1213.2341 (M + Na)+ | 1190 | 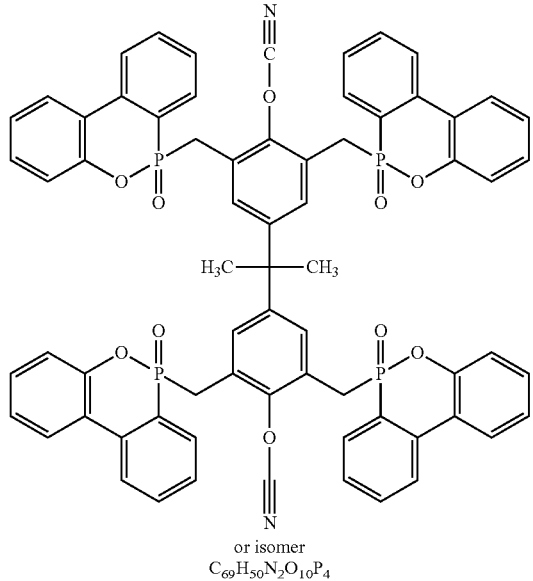<br>or isomer<br>$C_{69}H_{50}N_2O_{10}P_4$<br>1190.24159 Da |
| G(cyanate) | 1046.2740 (M + Na)+ | 1023 | 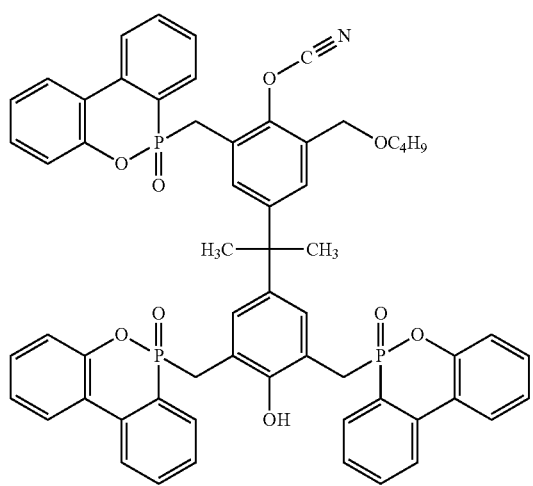<br>or isomer<br>$C_{60}H_{52}NO_9P_3$<br>1023.28549 Da |

TABLE 2-continued

Assignments from ESI Analysis of the Polycyanate of DOP-BN

| Compound ID | m/z Obsrvd Pos Ion | Nom MW | Tentative Assignments |
|---|---|---|---|
| H(dicyanate) | 1071.2723 (M + Na)+ | 1048 | 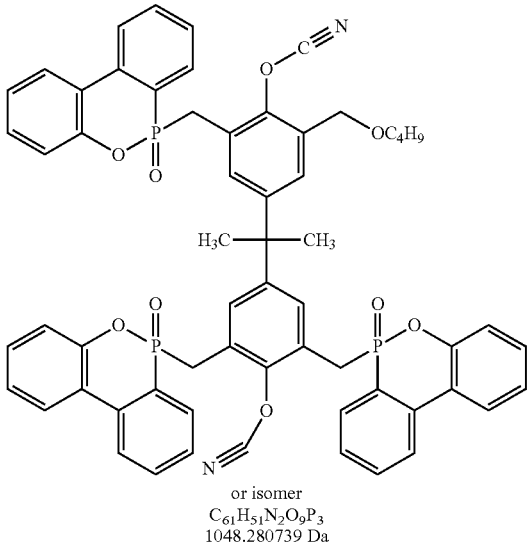<br>or isomer<br>$C_{61}H_{51}N_2O_9P_3$<br>1048.280739 Da |
| I(cyanate) | 904.3154 (M + Na)+ | 881 | 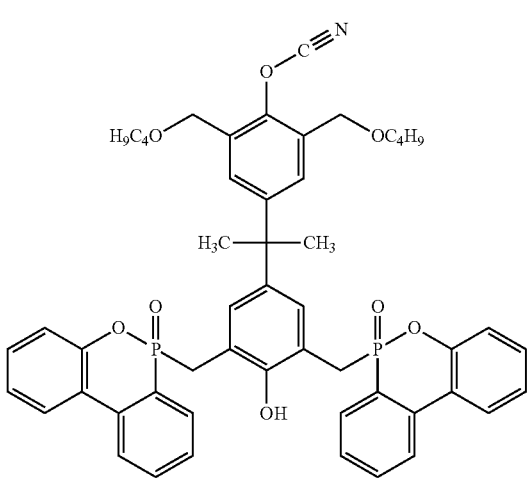<br>or isomer<br>$C_{52}H_{53}NO_8P_2$<br>881.32464 Da |

Example 2

Synthesis of the Homopolytriazine of the Polycyanate of DOP-BN

Differential scanning calorimetry (DSC) analysis (TA Instruments 2920 DSC) of portions (4.5, 5.3 and 7.7 milligrams) of the polycyanate of DOP-BN from Example 1 above was completed using a rate of heating of 7° C. per minute from 25° C. to 350° C. under a stream of nitrogen flowing at 35 cubic centimeters per minute. The data collected from the three DSC analyses was averaged. A single exotherm attributed to cyclotrimerization was detected with a 237.4° C. maximum accompanied by an enthalpy of 232.1 joules per gram. The onset temperature for this cyclotrimerization exotherm was 180.2° C. A second scanning of the resultant homopolytriazine revealed no further exothermicity indicative of curing. The homopolytriazine recovered from the DSC analysis was a transparent, amber colored, rigid solid.

Example 3

A. Preparation of a Blend of Polycyanate of DOP-BN and Bisphenol A Dicvanate

A portion (0.0176 gram, 15.0 weight %) of the polycyanate of DOP-BN from Example 1 and bisphenol A dicyanate (0.0996 gram, 85.0 weight %) were combined and finely ground together to provide a homogeneous solid.

B. Copolymerization of the Polycyanate of DOP-BN and Bisphenol A Dicyanate

Differential scanning calorimetry (DSC) analysis (TA Instruments 2920 DSC) of portion (8.0 and 9.0 milligrams) of the blend of the polycyanate of DOP-BN from Example 1 and bisphenol A dicyanate from part A of Example 3 (above) was completed using a rate of heating of 7° C. per minute from 25°

C. to 350° C. under a stream of nitrogen flowing at 35 cubic centimeters per minute. The data collected from the pair of DSC analyses was averaged. A single endotherm attributable to melting was detected at a 81.5° C. minimum accompanied by an enthalpy of 88.9 joules per gram. A single exotherm attributed to cyclotrimerization was detected with a 269.1° C. maximum accompanied by an enthalpy of 577.5 joules per gram. The onset temperature for this cyclotrimerization exotherm was 238.6° C. A second scanning of the resultant copolytriazine revealed a glass transition temperature of 216.0° C., with an exothermic shift at 265.8° C. indicative of further curing. The copolytriazine recovered from the DSC analysis was a transparent, amber colored, rigid solid.

Comparative Example A

Synthesis of the Homopolytriazine of the Dicyanate of Bisphenol A

Differential scanning calorimetry (DSC) analysis (TA Instruments 2920 DSC) of a portion (8.4 milligrams) of the bisphenol A dicyanate (same product used in Example 3 above) was completed using a rate of heating of 7° C. per minute from 25° C. to 350° C. under a stream of nitrogen flowing at 35 cubic centimeters per minute. The data collected from the pair of DSC analyses was averaged. A single endotherm attributable to melting was detected at a 83.6° C. minimum accompanied by an enthalpy of 103.8 joules per gram. A single exotherm attributed to cyclotrimerization was detected with a 323.0° C. maximum accompanied by an enthalpy of 550.2 joules per gram. The onset temperature for this cyclotrimerization exotherm was 305.1° C. A second scanning of the resultant homopolytriazine revealed a glass transition temperature of 208.1° C., with an exothermic shift at 267.2° C. indicative of further curing. The homopolytriazine recovered from the DSC analysis was a transparent, amber colored, rigid solid.

Example 4

A. Preparation of a Blend of Polycyanate of DOP-BN and 4,4'-bis(Maleimido)diphenylmethane Using a 4:1 Cyanate:Maleimide Equivalent Ratio A portion (0.2214 gram, 0.00043 cyanate equivalent) of the polycyanate of DOP-BN of Example 1 and 4,4'-bis(maleimido)diphenylmethane (0.0192 gram, 0.000107 maleimide equivalent) were combined and finely ground together to provide a homogeneous solid.

B. Copolymerization of the Polycyanate of DOP-BN and 4,4'-bis(Maleimido)diphenylmethane Differential scanning calorimetry (DSC) analysis (TA Instruments 2920 DSC) of portion (6.4 milligrams) of the blend of the polycyanate of DOP-BN and 4,4'-bis(maleimido)diphenylmethane from A above was completed using a rate of heating of 7° C. per minute from 25° C. to 325° C. under a stream of nitrogen flowing at 35 cubic centimeters per minute. A single exotherm attributed to copolymerization was detected with a 235.0° C. maximum accompanied by an enthalpy of 142.5 joules per gram. The onset temperature for this copolymerization exotherm was 141.4° C. A second scanning of the resultant copolymer revealed a glass transition temperature of 173.4° C., with an exothermic shift at 211.1° C. indicative of further curing. The bismaleimide triazine copolymer recovered from the DSC analysis was a transparent, amber colored, rigid solid.

Example 5

A. Preparation of a Blend of Polycyanate of DOP-BN and 4,4'-bis(Maleimido)diphenylmethane Using a 2:1 Cyanate:Maleimide Equivalent Ratio A portion (0.2192 gram, 0.000426 cyanate equivalent) of the polycyanate of DOP-BN from Example 1 and 4,4'-bis(maleimido)diphenylmethane (0.0381 gram, 0.000213 maleimide equivalent) were combined and finely ground together to provide a homogeneous solid.

B. Copolymerization of the Polycyanate of DOP-BN and 4,4'-bis(Maleimido)diphenylmethane Differential scanning calorimetry (DSC) analysis (TA Instruments 2920 DSC) of portion (7.5 milligrams) of the blend of the polycyanate of DOP-BN and 4,4'-bis(maleimido)diphenylmethane from A above was completed using a rate of heating of 7° C. per minute from 25° C. to 325° C. under a stream of nitrogen flowing at 35 cubic centimeters per minute. A single exotherm attributed to copolymerization was detected with a 236.4° C. maximum accompanied by an enthalpy of 185.0 joules per gram. The onset temperature for this copolymerization exotherm was 146.2° C. A second scanning of the resultant copolymer revealed a glass transition temperature of 180.3° C. The second scanning revealed no further exothermicity indicative of curing. (note: A second weaker apparent glass transition temperature was observed at 259.5° C.). A third scanning of the resultant copolymer revealed a glass transition temperature of 180.3° C. The third scanning revealed no further exothermicity indicative of curing. (note: A second weaker apparent glass transition temperature was observed at 260.9° C.). The bismaleimide triazine copolymer recovered from the DSC analysis was a transparent, amber colored, rigid solid.

Example 6

A. Preparation of a Blend of Polycyanate of DOP-BN and 4,4'-bis(Maleimido)diphenylmethane Using a 1.33:1 Cyanate:Maleimide Equivalent Ratio A portion (0.2299 gram, 0.000446 cyanate equivalent) of the polycyanate of DOP-BN from Example 1 and 4,4'-bis(maleimido)diphenylmethane (0.0599 gram, 0.000335 maleimide equivalent) were combined and finely ground together to provide a homogeneous solid.

B. Copolymerization of the Polycyanate of DOP-BN and 4,4'-bis(Maleimido)diphenylmethane Differential scanning calorimetry (DSC) analysis (TA Instruments 2920 DSC) of portion (7.0 milligrams) of the blend of the polycyanate of DOP-BN and 4,4'-bis(maleimido)diphenylmethane from A above was completed using a rate of heating of 7° C. per minute from 25° C. to 325° C. under a stream of nitrogen flowing at 35 cubic centimeters per minute. A single exotherm attributed to copolymerization was detected with a 236.8° C. maximum accompanied by an enthalpy of 188.9 joules per gram. The onset temperature for this copolymerization exotherm was 146.4° C. A second scanning of the resultant copolymer revealed a glass transition temperature of 191.4° C., with an exothermic shift at 267.4° C. indicative of further curing. The bismaleimide triazine copolymer recovered from the DSC analysis was a transparent, amber colored, rigid solid.

Example 7

A series of experiments were conducted to determine the impact of replacing DOP-BN with the polycyanate of DOP-BN mixtures of epoxy resins and bismaleimide-triazine resins (a BT-epoxy system). The BT-epoxy system included D.E.N.™ 438, 4,4'-bis(maleimido)diphenylmethane, N-phenylmaleimide, Primaset™ BA-230s (a partially trimerized bisphenol A cyanate ester), DOP-BN or the polycyanate of DOP-BN and 2-butanone as the solvent. The D.E.N.™ 438—maleimide—Primaset™ BA-230s equivalent weight ratios were constant throughout the Examples. This was done to isolate the effects of 1) replacing the phenolic functionality of the DOP-BN with the cyanate ester version, and 2) varying the amount of the DOP-BN or DOP-BN cyanate ester in the formulation.

Comparative examples were compounded utilizing DOP-BN at loading levels resulting in 1 wt.%, 2 wt.%, and 3 wt.% phosphorus in the solids portion of the formulation. Due to the increase in equivalent weight as a result of the additional carbon and nitrogen atoms resulting in the cyanate ester, the equivalent weight, as well as the percent phosphorus was adjusted for the calculations. The baseline percent phosphorus for the DOP-BN was estimated at 9.8% by weight. A value of 9.6% by weight was used for the polycyanate of DOP-BN.

Properties of interest were stroke gel time (tested according to ASTM D4640-86), Gardner Bubble Viscosity at time=0 (t0 hours) and time=24 hours (t24 hours) (tested according to ASTM D1545-07) (BYK-Gardner, GmbH) (ASTM D4640-86), glass transition temperature via DSC (tested according to ASTM D3418), and 5% decomposition temperature via thermogravimetric analysis (TGA), (tested according to ASTM E1131).

Masterblends

Masterblend A

Masterblend A was prepared as described above in Example 1.

Masterblend B

To a 30 mL scintillation vial was added 8.25 g of the solid DOP-BN of Example 1 and 6.75 g of 2-butanone. The vial was placed on a shaker overnight on low speed.

Masterblend C

To a 30 mL scintillation vial was added 8.25 g of the polycyanate of DOP-BN from Example 1 and 6.75 g of 2-butanone. The vial was placed on a shaker overnight on low speed.

Masterblend D

To a 30 mL scintillation vial was added 0.5 g of zinc hexanoate and 9.95 g of 2-butanone.

Formulation of Examples and Comparative Examples

Note: All samples were adjusted to 70% solids by weight and were dark amber and free from particulates or turbidity.

Comparative Example B

To a 30 mL scintillation vial was added 7.74 g of Masterblend A, 4.05 g of Primaset™ BA-230s, 1.95 g of Masterblend B, 0.66 g of 2-butanone, and 0.0419 g of Masterblend D. The sample was placed on a shaker for 90 minutes on low speed.

Comparative Example C

To a 30 mL scintillation vial was added 6.85 g of Masterblend A, 3.59 g of Primaset™ BA-230s, 3.90 g of Masterblend B, 1.27 g of 2-butanone, and 0.0399 g of Masterblend D. The sample was placed on a shaker for 90 minutes on low speed.

Comparative Example D

To a 30 mL scintillation vial was added 5.07 g of Masterblend A, 3.13 g of Primaset™ BA-230s, 5.84 g of Masterblend B, and 0.0340 g of Masterblend D. The sample was placed on a shaker for 90 minutes on low speed.

Example 8

To a 30 mL scintillation vial was added 7.72 g of Masterblend A, 4.04 g of Primaset™ BA-230s, 1.99 g of Masterblend C, 1.25 g of 2-butanone, and 0.0448 g of Masterblend D. The sample was placed on a shaker for 90 minutes on low speed.

Example 9

To a 30 mL scintillation vial was added 6.82 g of Masterblend A, 3.57 g of Primaset™ BA-230s, 3.98 g of Masterblend C, 0.64 g of 2-butanone, and 0.0395 g of Masterblend D. The sample was placed on a shaker for 90 minutes on low speed.

Example 10

To a 30 mL scintillation vial was added 5.93 g of Masterblend A, 3.10 g of Primaset™ BA-230s, 5.97 g of Masterblend C, and 0.0405 g of Masterblend D. The sample was placed on a shaker for 90 minutes on low speed.

Analysis

Approximately 2 mL of each sample was placed on a 171° C. hot plate to determine the gel point via the stroke cure method according to ASTM D4640-86. The gelled samples were removed from the hot plate, placed in an aluminum dish, and then placed into a 220° C. convection oven for 120 minutes for post cure. After 120 minutes, the samples were removed from the oven prepared for glass transition temperature ($T_g$) and decomposition temperature ($T_d$). The $T_g$ was determined via differential scanning calorimetry using a TA Instruments 2920 DSC under nitrogen with a flow rate of 35 cc/minute. The test method consisted of a temperature ramp from 60° C. to 275° C. at a 20° C./minute ramp rate under a nitrogen flow of 50 cc/minute. The $T_g$ was calculated utilizing the half extrapolated tangents method across the step transition. The $T_d$ was determined via thermogravimetric analysis using a TA Instruments Q50 TGA. The test method consisted of a temperature ramp from 25° C. to 450° C. at a 10° C./minute ramp rate under a nitrogen flow of 50 cc/minute. The 5% weight loss was calculated using the Value at Y function.

TABLE 3

Properties of Examples and Comparative Examples

| Property | Comparative Example A | Comparative Example B | Comparative Example C | Example 8 | Example 9 | Example 10 |
|---|---|---|---|---|---|---|
| Phosphorus Level (wt %) | 1 | 2 | 3 | 1 | 2 | 3 |
| t0 Hour Viscosity (Gardner Bubble Viscosity) | A | B | C | A | A | B |
| t24 Hour Viscosity (Gardner Bubble Viscosity) | A | C | D | A | A | B |
| t48 Hour Viscosity (Gardner Bubble Viscosity) | B | C | F | A | B | C |
| t120 Hour Viscosity (Gardner Bubble Viscosity) | C | E | I | B | B | C |
| Stroke Gel Time at 171° C. (minutes:seconds) | 3:52 | 4:17 | 4:49 | 5:08 | 7:03 | 8:30 |
| Glass Transition Temperature via DSC (60° C. to 275° C. at 20° C./minute, ° C.) | 222.47 | 212.94 | 197.43 | 233.36 | 224.65 | 219.87 |
| 5% Decomposition Temperature via TGA (25° C. to 275° C. at 10° C./minute, ° C.) | 359.54 | 362.11 | 355.85 | 363.66 | 359.77 | 352.88 |

The data in Table 3 demonstrates the increase in the glass transition temperature (Tg) and improved stability of the compositions containing the cyanate ester derivative of DOP-BN especially at higher phosphorus weight percent levels.

We claim:

1. A thermosetting monomer comprising at least two of an aryl-cyanato group and at least two of a phosphorus group, where the thermosetting monomer is represented by a compound of Formula (I):

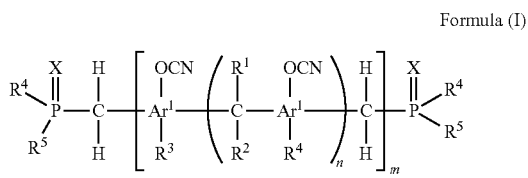

Formula (I)

wherein m is an integer from 1 to 20;
wherein n is an integer from 0 to 20 with the proviso that when n is 0 then m is an integer from 2 to 20;
wherein X is selected from the group consisting of sulfur, oxygen, and a lone electron pair;
wherein each $R^1$ and $R^2$ is independently a hydrogen, an aliphatic moiety having 1 to 20 carbon atoms, or aromatic hydrocarbon moiety having 6 to 20 carbon atoms, where the aliphatic moiety and the aromatic hydrocarbon moiety can be joined to form a cyclic structure;
wherein $R^3$ is selected from the group consisting of a hydrogen, an aliphatic moiety having 1 to 20 carbon atoms, an aromatic hydrocarbon moiety having 6 to 20 carbon atoms, $R^4R^5P(=X)CH_2$—, and $ROCH_2$—, where R is an aliphatic moiety having 1 to 20 carbon atoms; and
wherein each $R^4$ and $R^5$ is inde endentl an aliphatic moiety havin 1 to 20 carbon atoms, an aromatic hydrocarbon moiety having 6 to 20 carbon atoms, where the aliphatic moiety and the aromatic hydrocarbon moiety can be joined to form a cyclic structure, RX—, or wherein $R^4$ and $R^5$ together are $Ar^2X$—; and
wherein each $Ar^1$ and $Ar^2$ is independently a benzene, a naphthalene, or a biphenyl.

2. The thermosetting monomer of claim 1, wherein for the compound of Formula (I) X is oxygen, n is 1, m is 1, each $R^1$ and $R^2$ is a methyl group, $R^3$ is $R^4R^5P(=X)CH_2$—, and $R^4$ and $R^5$ together are $Ar^2X$, wherein $Ar^2$ is biphenyl such that $R^4R^5P(=X)$— is represented by a compound of Formula (II):

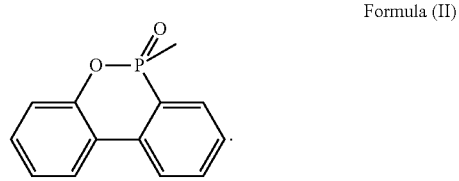 [SMILES: CP1(=O)Oc2ccccc2-c2ccccc21]

Formula (II)

3. The thermosetting monomer of claim 1, wherein for the compound of Formula (I) X is oxygen, n is 0, m is 2 or 3, $R^3$ is $R^4R^5P(=X)CH_2$—, and $R^4$ and $R^5$ together are $Ar^2X$, wherein $Ar^2$ is biphenyl such that $R^4R^5P(=X)$— is represented by a compound of Formula (II):

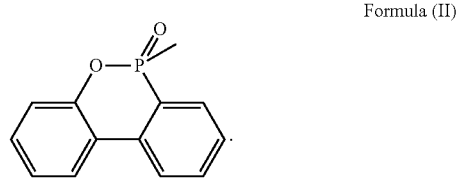 [SMILES: CP1(=O)Oc2ccccc2-c2ccccc21]

Formula (II)

4. The thermosetting monomer of claim 1, where $Ar^1$ is benzene.

5. A composition, comprising:
a formulation component selected from the group consisting of an epoxy resin, bismaleimide-triazine resin, a maleimide resin, a cyanate ester resin and combinations thereof; and
a thermosetting monomer comprising at least two of an aryl-cyanato group and at least two of a phosphorus group, where the thermosetting monomer is represented by a compound of Formula (I):

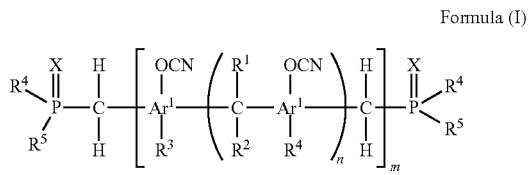

Formula (I)

wherein m is an integer from 1 to 20;

wherein n is an integer from 0 to 20 with the proviso that when n is 0 then m is an integer from 2 to 20;

wherein X is selected from the group consisting of sulfur, oxygen, and a lone electron pair;

wherein each $R^1$ and $R^2$ is independently a hydrogen, an aliphatic moiety having 1 to 20 carbon atoms, or aromatic hydrocarbon moiety having 6 to 20 carbon atoms, where the aliphatic moiety and the aromatic hydrocarbon moiety can be joined to form a cyclic structure;

wherein $R^3$ is selected from the group consisting of a hydrogen, an aliphatic moiety having 1 to 20 carbon atoms, an aromatic hydrocarbon moiety having 6 to 20 carbon atoms, $R^4R^5P(=X)CH_2$—, and $ROCH_2$—, where R is an aliphatic moiety having 1 to 20 carbon atoms; and wherein each $R^4$ and $R^5$ is independently an aliphatic moiety having 1 to 20 carbon atoms, an aromatic hydrocarbon moiety having 6 to 20 carbon atoms, where the aliphatic moiety and the aromatic hydrocarbon moiety can be joined to form a cyclic structure, RX—, or wherein $R^4$ and $R^5$ together are $Ar^2X$—; and wherein each $Ar^1$ and $Ar^2$ is independently a benzene, a naphthalene, or a biphenyl.

6. The composition of claim 5, where the maleimide resin is bismaleimide of 4,4'-diaminodiphenylmethane.

7. The composition of claim 5, where the composition has a phosphorus content of 0.1 to 3.5 weight percent.

8. The composition of claim 5, where the composition has an onset to cure temperature of 180.2° C. and a cure enthalpy of 232.1 joules per gram of the composition.

9. The composition of claim 8, where the composition is fully cured after a single exotherm at 237.4° C.

10. A process for making a thermosetting monomer, comprising:

condensing an etherified resole with (H—P(=X)$R^4R^5$) to form a reaction product, wherein each $R^4$ and $R^5$ is independently an aliphatic moiety having 1 to 20 carbon atoms, an aromatic hydrocarbon moiety having 6 to 20 carbon atoms, where the aliphatic moiety and the aromatic hydrocarbon moiety can be joined to form a cyclic structure, RX—, or wherein $R^4$ and $R^5$ together are $Ar^2X$—; wherein X is sulfur, oxygen, or a lone electron pair; and wherein $Ar^2$ is benzene, naphthalene, or biphenyl; and converting the reaction product to the thermosetting monomer with a cyanogen halide and a base, where the thermosetting monomer is represented by a compound of Formula (I):

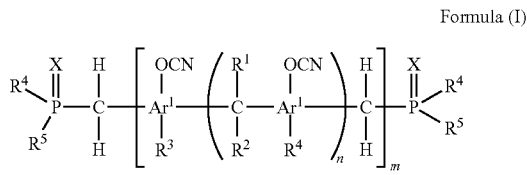

Formula (I)

wherein m is an integer from 1 to 20;

wherein n is an integer from 0 to 20 with the proviso that when n is 0 then m is an integer from 2 to 20;

wherein X is selected from the group consisting of sulfur, oxygen, and a lone electron pair;

wherein each $R^1$ and $R^2$ is independently a hydrogen, an aliphatic moiety having 1 to 20 carbon atoms or aromatic hydrocarbon moiety having 6 to 20 carbon atoms, where the aliphatic moiety and the aromatic hydrocarbon moiety can be joined to form a cyclic structure;

wherein $R^3$ is selected from the group consisting of a hydrogen, an aliphatic moiety having 1 to 20 carbon atoms, an aromatic hydrocarbon moiety having 6 to 20 carbon atoms, $R^4R^5P(=X)CH_2$—, and $ROCH_2$—, where R is an aliphatic moiety having 1 to 20 carbon atoms; and wherein each $R^4$ and $R^5$ is independently an alphatic moirty having 1 to 20 carbon atoms, an aromatic hydrocarbon moiety having 6 to 20 carbon atoms, where the aliphatic moiety and the aromatic hydrocarbon moiety can be joined to form a cyclic structure, RX—, or wherein $R^4$ and $R^5$ together are $Ar^2X$—; and wherein each $Ar^1$ and $Ar^2$ is independently a benzene, a naphthalene, or a biphenyl.

11. The process of claim 10, wherein $R^4$ and $R^5$ together are $Ar^2X$—, X is oxygen and $Ar^2$ is biphenyl to give 9,10-dihydro-9-oxa-10-phosphaphenanthrene 10-oxide.

12. The process of claim 10, wherein the etherified resole is a butyl ether bisphenol-A resole, the cyanogen halide is cyanogen bromide, and the base is triethylamine.

* * * * *